United States Patent [19]
Calderwood et al.

[11] Patent Number: 5,747,028
[45] Date of Patent: May 5, 1998

[54] **IMMUNIZING COMPOSITIONS COMPRISING *VIBRIO CHOLERAE* EXPRESSING HETEROLOGOUS ANTIGENS**

[75] Inventors: Stephen B. Calderwood, Wellesley; Joan R. Butterton, Newton; John J. Mekalanos, Cambridge, all of Mass.

[73] Assignee: The President and Fellows of Harvard College, Cambridge, Mass.

[21] Appl. No.: 480,510

[22] Filed: Jun. 7, 1995

Related U.S. Application Data

[63] Continuation of Ser. No. 20,501, Feb. 22, 1993, abandoned.
[51] Int. Cl.$^6$ .......................... C12N 1/21; A61K 39/106
[52] U.S. Cl. .................. 424/93.2; 435/69.1; 435/69.3; 435/252.3
[58] Field of Search ...................... 435/69.1, 252.3, 435/69.3; 424/93.2

[56] References Cited

U.S. PATENT DOCUMENTS 4,882,278  11/1989  Mekalanos ........................ 435/172.3

FOREIGN PATENT DOCUMENTS

| | | |
|---|---|---|
| 0 251 579 | 1/1988 | European Pat. Off. . |
| 0 257 837 | 3/1988 | European Pat. Off. . |
| 0 322 237 | 6/1989 | European Pat. Off. . |
| 0 564 689 | 10/1993 | European Pat. Off. . |
| WO89/02924 | 4/1989 | WIPO . |
| WO 90/03437 | 4/1990 | WIPO . |
| WO 91/18092 | 11/1991 | WIPO . |
| WO 94/00493 | 1/1994 | WIPO . |
| WO 94/01533 | 1/1994 | WIPO . |

OTHER PUBLICATIONS

Acheson et al., Protective Immunity to Shiga–Like Toxin I Following Oral Immunization with Shiga–Like Toxin I B–Subunit–Producing *Vibrio cholerae* CVD 103–HgR, Infection and Immunity 64:355–357, 1996.

Bäckström et al., Insertion of a HIV–1–Neutralizing Epitope in a Surface–Exposed Internal Region of the Cholera toxin B–subunit, Gene pp. 211–217, 1994.

Jobling et al., Fusion Proteins Containing the A2 Domain of Cholera Toxin Assemble with B Polypeptides of Cholera Toxin to Form Immunoreactive . . . Holotoxin–Like Chimeras, Infection & Immunity 60:4915–4924, 1992.

Kaper and Levine, Recombinant Attenuated *Vibrio cholerae* Stains Used as Live Oral Vaccines, Res. Microbiol. 141:901–906, 1990.

Kaper et al., A Recombinant Live Oral Cholera Vaccine, Bio/Technology 345–349, Apr. 1984.

Pierce et al., Determinants of the Immunogenicity of Live Virulent and Mutant *Vibrio cholerae* O1 in Rabbit Intestine, Infection and Immunity 55:477–481, 1987.

Sanchez et al., Genetic Fusion of a Non–toxic Heat–Stable Enterotoxin–Related Decapeptide Antigen to Cholera Toxin B–subunit, FEBS Letters 241:110

OTHER PUBLICATIONS

Keren et al., Direct Demonstration in Intestinal Secretions of an IgA Memory Response to Orally Administered *Shigella flexneri* Antigens, J. Immun. 128:475–479, 1982.

Bjorn et al., Effect of Iron on Yields of Exotoxin A in Cultures of *Pseudomonas aeruginosa* PA–103, Infec. Immun. 19:785–791, 1978.

Black et al., Protective Efficacy in Humans of Killed Whole-Vibrio Oral Cholera Vaccine with and without the B Submit of Cholera Toxin, Infec. Immun. 55:1116–1120, 1987.

Blomfield et al., Allelic Exchange in *Escherichia coli* Using the *Bacillus subtilis* sacB Gene and a Temperature-Sensitive pSC101 Replicon, Mol. Micro. 5:1447–1457, 1991.

Calderwood et al., Nucleotide Sequence of the Shiga-Like Toxin Genes of *Escherichia coli*, Proc. Natl. Acad. Sci. USA 84:4364–4368, 1987.

Calderwood et al., A System for Production and Rapid Purification of Large Amounts of the Shiga Toxin/Shiga--Like Toxin I B Subunit, Infec. Immun. 58:2977–2982, 1990.

Calderwood and Mekalanos, Iron Regulation of Shiga-Like Toxin Expression in *Escherichia coli* Is Mediated By the Fur Locus, J. Bac. 169:4759–4764, 1987.

Clemens et al., Impact of B Subunit Killed Whole-Cell and Killed Whole-Cell-Only Oral Vaccines . . . Illness and Mortality in an Area Endemic for Cholera, Lancet 1:375–1379, 1988.

Czerkinsky et al., Antibody-Producing Cells in Peripheral Blood and Salivary Glands after Oral Cholera Vaccination of Humans, Infec. Immun. 59:996–1001, 1991.

Daskaleros et al., Iron Uptake in *Plesiomonas shigelloides*: Cloning of the Genes for the Heme-Iron Uptake System, Infec. Immun. 59:2706–2711, 1991.

De Grandis et al., Nucleotide Sequence and Promoter Mapping of the *Escherichia coli* Shiga-Like Toxin Operon of Bacteriophage H–19B, J. Bac. 169:4313–4319, 1987.

De Lorenzo et al., Operator Sequences of the Aerobactin Operon of Plasmid ColV–K30 Binding the Ferric Uptake Regulation (fur) Repressor, J. Bac. 169:2624–2630, 1987.

Donnenberg and Kaper et al., construction of an eae Deletion Mutant of Enteropathogenic *Escherichia coli* By Using a Positive-Selection Suicide Vector, Infec. Immun. 59:4310–4317, 1991.

Donohue–Rolfe et al., Pathogenesis of Shigella Diarrhea, J. Exp. Med. 160:1767–1781, 1984.

Donohue–Rolfe et al., Enzyme–Linked Immunosorbent Assay for Shigella Toxin, J. Clin. Micro. 24:65–68, 1986.

Fernandez-Beros et al., Immune Response to the Iron-Deprivation-Induced Proteins of *Salmonella typhi* in Typhoid Fever, Infec. Immun. 57:1271–1275, 1989.

Gentry et al., Quantitative Microtiter Cytotoxicity Assay for Shigella Toxin, J. Clin. Micro. 12:361–366, 1980.

Goldberg et al., Identification of an Iron-Regulated Virulence Determinant in *Vibrio cholerae*, Using TnphoA Mutagenesis, Infec. Immun. 58:55–60, 1990.

Goldberg et al., Positive Transcriptional Regulation of an Iron-Regulated Virulence Gene in *Vibrio cholerae*, Proc. Natl. Acad. Sci. USA 88:1125–1129, 1991.

Goldberg et al., Transcriptional Regulation by Iron of a *Vibrio cholerae* Virulence Gene and Homology of the *Escherichia coli* Fur System, J. Bac. 172:6863–6870, 1990.

Goldberg et al., Characterization of a *Vibrio cholerae* Virulence Factor Homologous to the Family of TonB–Dependent Proteins, Mol. Micro. 6:2407–2418, 1992.

Harari et al., Synthetic Peptides of Shiga Toxin B Subunit Induce Antibodies Which Neutralize its Biological Activity, Infec. Immun. 56:1618–1624, 1988.

Harari and Arnon et al., Carboxy-Terminal Peptides from the B subunit of Shiga Toxin Induce a Local and Parenteral Protective Effect, Mol. Immun. 27:613–621, 1990.

Herrington et al., Toxin, Toxin–Coregulated Pili, and the toxR Regulon are Essential for *Vibrio cholerae* Pathogenesis in Humans, J. Exp. Med. 168:1487–1492, 1988.

Köster et al., Molecular Characterization of the Iron Transport System Mediated by the pJM1 Plasmid in *Vibrio anguillarum* 775, J. Biol. Chem. 266:23829–23833, 1991.

Levine et al., Safety, Immunogenicity, and Efficacy of Recombinant Live Oral Cholera Vaccines, CVD 103 and CVD 103–HgR, Lancet 2:467–470, 1988.

Harford et al., Cholera Toxin Genes: Nucleotide Sequence, Deletion Analysis and Vaccine Development, Nature 306:551–557, 1983.

Owen et al., M Cell Transport of *Vibrio cholerae* from the Intestinal Lumen into Peyer's Patches:A Mechanism for Antigen Sampling and for Microbial Transepithelial Migration, J. Infec. Dis. 153:1108–1118, 1986.

Pearson et al., New Attenuated Derivatives of *Vibrio cholerae*, Res. Microbiol. 141:893–899, 1990.

Poole and Braun, Iron Regulation of *Serratia marcescens* Hemolysin Gene Expression, Infec. Immun. 56:2967–2971, 1988.

Staggs and Perry, Fur Regulation in Yersinia Species, Mol. Microbiol. 6:2507–2516, 1992.

Staggs and Perry, Identification and Cloning of a Fur Regulatory Gene in *Yersinia pestis*, J. Baciol. 173:417–425, 1991.

Svennerholm et al., Intestinal Antibody Responses After Immunization with Cholera B Subunit, Lancet 1:305–308, 1982.

Svennerholm et al., Mucosal Antitoxic and Antibacterial Immunity after Cholera Disease and After Immunization with a Combined B Subunit–Whole Cell Vaccine, J. Infec. Dis. 149:884–893, 1984.

Winner III et al., New Model for Analysis of Mucosal Innumity: . . . Hybridoma Tumors Protects Against *Vibrio cholerae* Infection, Infec. Immun. 59:977–982, 1991.

Abstracts of the 89th Annual Meeting of the American Society for Microbiology, p. 128, 1989, M. Dertzbaugh et al., abstract E–6.

Forrest et al., Immunogenicity of a Candidate Live Oral Typhoid/Cholera Hybrid Vaccine in Humans, J. Infectious Diseases 159:145:146, 1989.

Miller and Mekalanos, Strategies for the Development of Vaccines for Typhoid Fever, Shigellosis, and Cholera, Biomedical Science and the Third World 569:145–154, 1989.

Nashar et al., Current Progress in the Development of the B Subunits of Cholera Toxin and *Escherichia coli* Heat–labile Enterotoxin . . . the Oral Delivery of Heterologous Antigens and Epitopes, Vaccine 11:235–240, 1993.

Joan R. Butterton et al., Cloning, Sequencing, and Transcriptional Regulation of viuA, the Gene Encoding the Ferric Vibriobactin Receptor of *Vibrio cholerae*, Jun. 1992, Journal of Bacteriology, vol. 174, No. 11, pp. 3729–3738.

Dixon et. al 1983. The Biology of Immunologic Disease. pp. 331–338. Sinauer Associates, Inc., Sunderland, Massachusetts.

Jacobs et. al. 1987. Nature. vol. 327(11);532–534.

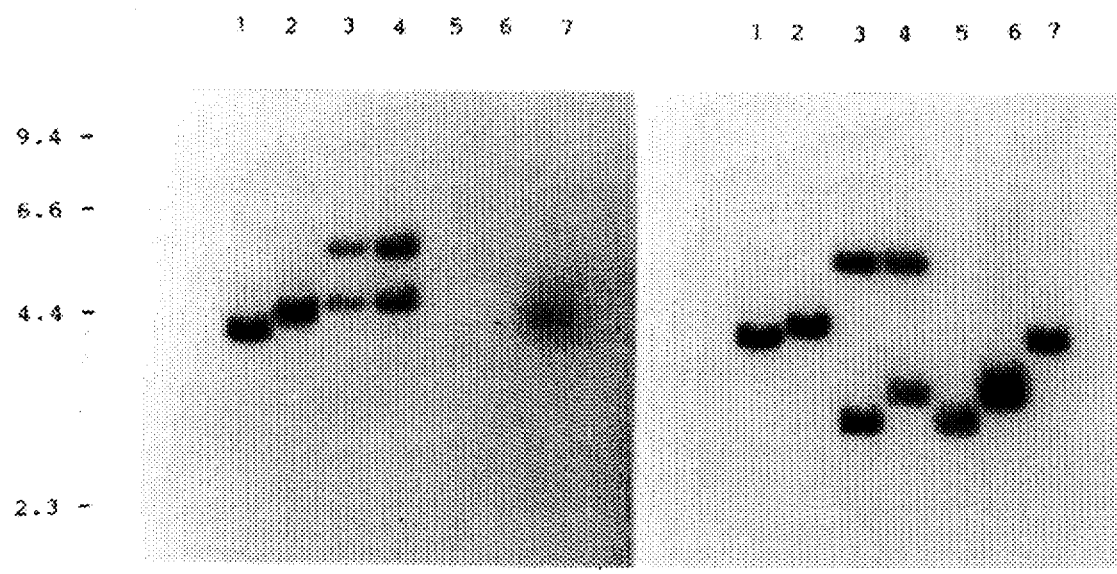
FIG. 2A　　　　FIG. 2B

```
                1060        1070        1080         1090        1100
ATAATTATCATTTAAAGGAGTGGTAA ATG TCC AGA TTC AAT CCA TCC CCC GTC AGT TTA
   ←――――――          SD     Met Ser Arg Phe Asn Pro Ser Pro Val Ser Leu 1120        1130        1140        1150        1160
TCT GTG ACA CTA GGC TTA ATG TTT TCG GCT AGC GCT TTT GCT CAA GAC GCG ACG
Ser Val Thr Leu Gly Leu Met Phe Ser Ala Ser Ala Phe Ala Gln Asp Ala Thr 1170        1180        1190        1200        1210
AAA ACG GAT GAA ACC ATG GTG GTC ACT GCG GCG GGA TAC GCG CAA GTG ATT CAA
Lys Thr Asp Glu Thr Met Val Val Thr Ala Ala Gly Tyr Ala Gln Val Ile Gln 1230        1240        1250   BglII 1260        1270
AAT GCA CCA GCC AGT ATC AGT GTG ATT TCA AGA GAA GAT CTG GAA TCT CGC TAT
Asn Ala Pro Ala Ser Ile Ser Val Ile Ser Arg Glu Asp Leu Glu Ser Arg Tyr 1280        1290        1300        1310        1320
TAC CGT GAT GTG ACC GAT GCG CTA AAA AGC GTA CCG GGT GTG ACA GTC ACC GGA
Tyr Arg Asp Val Thr Asp Ala Leu Lys Ser Val Pro Gly Val Thr Val Thr Gly 1330        1340        1350        1360        1370
GGG GGC GAT ACT ACC GAT ATC AGC ATT CGT GGT ATG GGA TCA AAC TAT ACT CTT
Gly Gly Asp Thr Thr Asp Ile Ser Ile Arg Gly Met Gly Ser Asn Tyr Thr Leu 1390        1400        1410        1420        1430
ATC TTG GTG GAT GGT AAG CGC CAA ACC TCA CGC CAG ACC CGT CCA AAC AGC GAT
Ile Leu Val Asp Gly Lys Arg Gln Thr Ser Arg Gln Thr Arg Pro Asn Ser Asp

SmaI          1450        1460        1470        1480
GGC CCG GGC ATT GAG CAA GGT TGG TTA CCG CCA CTG CAA GCG ATT GAA CGT ATC
Gly Pro Gly Ile Glu Gln Gly Trp Leu Pro Pro Leu Gln Ala Ile Glu Arg Ile 1500        1510        1520        1530
GAG GTG ATC CGT GGC CCG ATG TCT ACG CTG TAC GGC TCG GAT Gct gac ...
Glu Val Ile Arg Gly Pro Met Ser Thr Leu Tyr Gly Ser Asp Ala Asp
```

FIG. 5B

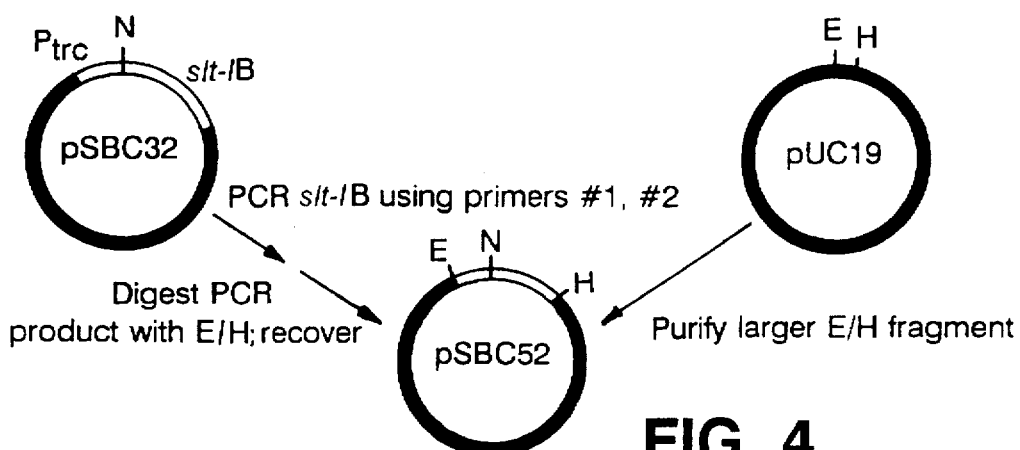

FIG. 4

```
    ClaI    10         20         30         40         50         60         70
ATCGATGATAAAAAATCCCGCTGCGGCGGGATTTTTTTATTGCCACTCATCGGGCCTTGCTTGGCGGAGCG 80         90        100        110        120        130        140
CATCAATAAATAGGCGCAGCCGAAGTGGGTGACGACCGAGCGGATAGAAGCAGTTGATTTCTGTTGGCTG

150    HincII    170        180        190        200        210
TGATTGCCATCCGTTGACGCAAGGAATGAGGCTGCCCGGATGCGCCGTTTCAAAACCATTGGCAAACCAA 220        230        240        250        260        270        280
GTGGGAAGCAAACCAATACCACGACCTTTAGCAATCGCATCGGCTTGCATGGCAAGATTATCGCTTTGTA 290        300        310        320        330        340        350
AACGACTCTCTAGTGCTGGCAGTGAATAACTGCCGAACTCTGGATGGTGCAGTTCAAGCTCCGCGCGCCG 360       NcoI    380        390        400        410        420
ACAAGCAATAAAATCAATCCATGGGTGATGAATCAGCTCACGAGGATGGGTCGGTTTATCTCGATGGGCC 430        440        450        460        470        480        490
AAATATTTGGGAGAGGCGTAAGTGGCATAGCGCCAATAGCCTAAGCGTTCTTTGCGATAACCCATGGGGG 500        510        520        530        540        550     AccI
CGGCGTGTTCAATCCAAATGATCAAATCGGGCTCAAACACCTCATCACTGTGTTGAAACTGGCTGAGTAG _     570        580        590        600        610        620        630
ACGGATCTTCAATGTCGAATGCTGCTGCATAAACTCATCCAATACTTGGCTGAGCCAGCCGCGGATCAAA 640        650        660        670        680        690        700
TTGGGGTGTACCACCAGCGTGAGTTCGCCAGTCACTTGATTGTTCAATTCTTGCAACGCTTCCTGACTTT BalI    720        730        740        750        760        770
TATTGGCCAGTTCAAGTAGTTGCTCCGAGTAAACCGCAAACACTTCTCCTGCTTTGGTGAGCGTTAAGCG 780        790        800        810        820        830        840
GTTGCCTTGACGCATCAACAAGCTTTGTCCCAAGTCCTCTTCAAGTTGCGCCAAACGGCGACTCAGGGTG 850        860        870        880        890        900    HindIII
GATTTAGGCTGTTCAAGCGCTTTGGCAGCGGCAGTCAGGCTCTTATGTTGGCAAAGCGCATGAAAGCTT 920 BglII 930        940        950        960        970        980
TTACGGCGCTGAGATCTTGCATAGGTATTTGACCCTTAAAGAATAATTACCACAGACGTTCCATATTTGG 990       1000       1010       1020       1030        *        1050
ACCGAACTATTCCATGTGTCGATCTATCTCCAGTACAGAATATATGAATAATCCGCTTCTCAAATTAAGA
                                                   -10
```

FIG. 5A

IMMUNIZING COMPOSITIONS COMPRISING *VIBRIO CHOLERAE* EXPRESSING HETEROLOGOUS ANTIGENS

This is a continuation of application Ser. No. 08/020,501, filed Feb. 22, 1993, now abandoned.

STATEMENT AS TO FEDERALLY SPONSORED RESEARCH

The work disclosed herein was supported in part by U.S. Public Health Service grant AI 27329 and a National Research Service Award from the National Institute of Allergy and Infectious Diseases.

The field of the invention is genetically engineered live bacterial cell vaccine strains.

BACKGROUND OF THE INVENTION

*V. cholerae* is a gram-negative bacterium that causes a severe, dehydrating and occasionally fatal diarrhea in humans. There are an estimated 5.5 million cases of cholera each year, resulting in greater than 100,000 deaths (Bull. W.H.O. 68:303–312, 1990). Over the last several decades, cholera has been considered to occur primarily in developing countries of Asia and Africa, but recently it has reached epidemic proportions in regions of South and Central America, as well (Tauxe et al., J. Am. Med. Assn. 267:1388–1390, 1992; Swerdlow et al., J. Am. Med. Assn. 267:1495–1499, 1992).

Patients who recover from cholera infection have long-lasting, perhaps lifelong, immunity to reinfection (Levine et al., J. Infect. Dis. 143:818–820, 1981). The development of *V. cholerae* vaccines has focused on reproducing this naturally occurring immunity, but the currently available parenteral, killed whole-cell vaccine preparation provides less than 50% protection from disease, for a duration of only 3 to 6 months (Saroso et al., Bull. W.H.O. 56:619–627, 1978; Levine et al., Microbiol. Rev. 47:510–550, 1983). A genetically-engineered, live oral vaccine for *V. cholerae* has several theoretical advantages over the present parenteral killed whole-cell vaccine. As a mucosal pathogen, *V. cholerae* adheres selectively to the M cells of the gastrointestinal tract (Owen et al., J. Infect. Dis. 153:1108–1118, 1986) and is a strong stimulus to the common mucosal immune system (Svennerholm et al., Lancet i:305–308, 1982); and oral cholera vaccination in humans produces a strong salivary gland IgA response to cholera toxin B subunit (Czerkinsky et al., Infect. Immun. 59:996–1001, 1991). Oral vaccines take advantage of the fact that oral administration of antigens appears to be the most efficient stimulus for the development of secretory IgA (Svennerholm, supra), and that secretory IgA by itself is sufficient to protect against intestinal disease from *V. cholerae* (Winner III, et al., Infect. Immun. 59:977–982, 1991). Oral, killed whole cell vaccines with or without the B subunit of cholera toxin have undergone extensive testing in volunteer and field trials over the past decade, and have been found to be more immunogenic and confer longer protection than the parenteral killed whole-cell vaccine (Svennerholm et al., J. Infect. Dis. 149:884–893, 1984; Black et al., Infect. Immun. 55:1116–1120, 1987; Clemens et al., Lancet i:1375–1378, 1988; Clemens et al., J. Infect. Dis. 158:60–69, 1988; Jertborn et al., J. Infect. Dis. 157:374–377, 1988; Sack et al., 164:407–11, 1991).

Such killed whole-cell vaccines were traditionally favored over live whole-cell vaccines because the latter, which can multiply in the gut of the vaccinated animal, were considered unsafe. However, unlike killed-cell vaccines, live-cell vaccines would not require multiple doses, and in a rabbit model, live bacteria are more effective immunogens for secretory IgA than dead organisms (Keren et al., J. Immunol. 128:475–479, 1982). Live vaccines have the further advantage of potentially being transmitted from recipients to others in the community, leading to herd immunity.

The most important virulence factor for *V. cholerae* in causing clinical disease is cholera toxin, a protein complex consisting of one A subunit and 5 B subunits. Live, oral vaccine strains currently being tested bear mutations in either the A subunit or in both subunits of cholera toxin (Mekalanos et al., Nature 306:551–557, 1983; Herrington et al., J. Exp. Med. 168:1487–1492, 1988; Levine et al., Lancet ii:467–470, 1988). An internal deletion of the gene encoding the A subunit of cholera toxin (ctxA) in the classical strain 0395 produces a strain (0395-N1) which is highly immunogenic in humans, but produces non-specific symptoms in about half of the recipients (Mekalanos, supra; Herrington, supra; Mekalanos, U.S. Pat. No. 4,882,278, herein incorporated by reference), an indication that the strain is still virulent.

SUMMARY OF THE INVENTION

As described in detail below, it has now been found that a *V. cholerae* gene, such as the irgA locus of *V. cholerae*, can function as a site for the integration and high-level expression of sequences encoding heterologous antigens in vaccine strains of *V. cholerae*. IrgA, the major iron-regulated outer membrane protein of *V. cholerae*, is a virulence factor for this organism that is independent of cholera toxin (Goldberg et al., U.S. Ser. No. 07/629,102, herein incorporated by reference; Goldberg et al., Infect. Immun. 58:55–60, 1990). In vivo-grown *V. cholerae* expresses iron-regulated proteins that are not seen following growth in normal in vitro conditions (Sciortino et al., 42:990–996, 1983), suggesting that the organisms sense low-iron conditions in the intestine. A mutation in irgA produces a 100-fold defect in the virulence of *V. cholerae* in a suckling mouse model. Regulation of irgA expression by iron is exceptionally tight, with a 1000-fold induction ratio in low- compared with high-iron conditions (Goldberg et al., Infect. Immun. 58:55–60, 1990). The entire structural gene of irgA has been cloned from the classical *V. cholerae* strain 0395 (Goldberg et al., Mol. Microbiol. 6:2407–2418, 1992). Use of such an iron-regulated promoter to control expression of a heterologous antigen in a live vaccine strain has a number of distinct advantages. A high induction ratio ensures that the gene encoding the heterologous antigen (1) will be expressed in the low-iron environment of the vaccinee's gut at a level high enough to ensure that it induces an immune response, and yet (2) will be expressed minimally when the cells are cultured in vitro, where high-level expression would potentially provide selection pressure favoring inactivation of the gene and complicate large-scale culturing of the cells necessary for vaccine production. Where, as in the case of irgA, the protein encoded by the naturally-occurring gene is, for at least some *V. cholerae* strains, a virulence factor that is not essential for growth of the bacterium, insertion of the heterologous antigen coding sequence next to the promoter can be readily accomplished in such a way as to delete or otherwise inactivate the virulence factor coding sequence, thereby decreasing the virulence of the engineered strain without affecting its viability.

The invention thus includes a genetically engineered *V. cholerae* chromosome containing a DNA sequence encoding a heterologous antigen, the DNA sequence being functionally linked to a naturally-occurring *V. cholerae* promoter. The heterologous antigen, defined as a polypeptide which is not expressed by the wildtype host species, is preferably a nontoxic polypeptide which is part or all of a protein that is naturally expressed by an infectious organism, and which induces an antigenic response in an animal (preferably a mammal such as a human, non-human primate, cow, horse, sheep, goat, pig, dog, cat, rabbit, rat, mouse, guinea pig, or hamster). The infectious organism from which the heterologous antigen is derived may be, for example, a bacterium, a virus, or a eukaryotic parasite, and the heterologous antigen may be, e.g., an OSP (Outer Surface Protein) of *Borelia burgdorferai*; animmunogenic, nontoxic subunit or fragment of a bacterial toxin such as Shiga toxin, diphtheria toxin, Pseudomonas exotoxin A, pertussis toxin, tetanus toxin, anthrax toxin, one of the *E. coli* heat-labile toxins (LTs), one of the *E. coli* heat-stable toxins (STs), or one of the *E. coli* Shiga-like toxins; an immunogenic portion of a viral capsid from a virus such as human immunodeficiency virus (HIV), any of the Herpes viruses (e.g., Herpes simplex virus or Epstein-Barr virus), influenza virus, poliomyelitis virus, measles virus, mumps virus, or rubella virus; or an immunogenic polypeptide derived from a eukaryotic parasite, such as the causative agent for malaria, pneumocystis pneumonia, or toxoplasmosis. (One preferred example of such a polypeptide is a malarial circumsporozoite protein.) By "functionally linked to a naturally-occurring *V. cholerae* promoter" is meant that expression of the sequence encoding the heterologous antigen is controlled by a promoter which is found in wild-type *V. cholerae*, such as the ctxA promoter, or an iron-regulated promoter such as that of irgA. Construction of such a functional linkage can be accomplished as described in detail below, or generally, using standard methods, by locating the desired promoter sequence sufficiently near to (and typically, though not necessarily, just upstream of) the promoterless heterologous antigen-encoding sequence to permit the desired promoter sequence to control expression of the latter sequence. Functional siting of promoter sequences is well within the abilities of one of ordinary skill in the art of prokaryotic gene expression. Where the promoter naturally controls the expression of a *V. cholerae* virulence factor that is nonessential for growth of the cell, the sequence encoding that virulence factor will preferably be deleted or otherwise mutated to prevent expression of a biologically active form of that virulence factor. Preferably, the ctxA locus on the chromosome will also be deleted or otherwise inactivated, so that biologically active cholera toxin cannot be expressed from the chromosome. Such deletions, mutations and insertions can readily be carried out by one of ordinary skill using the methods described herein, or other well-known, standard techniques. In preferred embodiments, the ctxA deletion is identical to that of strain 0395-N1 (Mekalanos, U.S. Pat. No. 4,882,278).

Also within the invention is a bacterial chromosome (preferably from a gram-negative, enteric bacterium such as *V. cholerae*), containing a DNA sequence encoding a heterologous antigen, which sequence is functionally linked to an iron-regulated promoter which functions in the host bacterium to permit significantly (i.e., at least ten-fold and preferably 100-fold) higher expression of the heterologous antigen in a low-iron environment, such as in an animal's intestine, than in a high-iron environment, such as under typical in vitro culture conditions. An example of such a promoter is the naturally-occurring promoter of *V. cholerae* irgA, which includes at a minimum a sequence substantially identical to nucleotides 1000 through 1041 (SEQ ID NO: 2), inclusive, of the sequence shown in FIG. 5 (SEQ ID NO: 1). The promoter sequence used is preferably nucleotides 922 to 1041 (SEQ ID NO: 3), more preferably 922 to 1079 (SEQ ID NO: 4) or 1000 to 1079 (SEQ ID NO: 5), still more preferably 905 to 1041 (SEQ ID NO: 6) or 905 to 1079 (SEQ ID NO: 7), and most preferably 905 to 1438 (SEQ ID NO: 8), 922 to 1438 (SEQ ID NO: 9), or 1000 to 1438 (SEQ ID NO: 10) (all inclusive). Examples of other iron-regulated promoters which would be useful in the invention are those derived from the fatA gene of *V. anquillarum* (Koster et al. J. Biol. Chem. 266:23829–23833, 1991); *E. coli* slt-IA (or other *E. coli* Fur-binding promoter sequences, as discussed by Calderwood et al., J. Bacteriol. 169:4759–4764, 1987; De Grandis et al., J. Bacteriol. 169:4313–4319, 1987; and DeLorenzo et al., J. Bacteriol. 169:2624–2630, 1987); the iron-regulated outer membrane proteins of *Salmonella typhi* (Fernandez et al., Infect. Immun. 57:1271–1275, 1989), the iron-regulated hemolysin promoter of Serratia (Poole et al., Infect. Immun. 56:2967–2971, 1988); the Yersenia iron-regulated promoters (Carniel et al., Molecular Microbiol. 6:379–388, 1992; Staggs et al., J. Bacteriol. 173:417–425, 1991; and Staggs et al., Molecular Microbiol. 6:2507–2516, 1992); the *V. vulnificus* iron-regulated promoters; the Pseudomonas exotoxin A iron-regulated promoter (Bjorn et al., Infect. Immun. 19:785–791, 1978); and Plesiomonas iron-regulated genes involved in heme-iron uptake (Daskaleros et al., Infect. Immun. 59:2706–2711, 1991). It is believed that most if not all enteric, gram-negative bacterial species, including *E. coli*, Salmonella, Shigella, Yersenia, Citrobacter, Enterobacter, Klebsiella, Morganella, Proteus, Providencia, Serratia, Vibrios, Plesiomonas, and Aeromonas, utilize highly similar fur-binding, iron-regulated promoter sequences, and it is likely that they also utilize secondary iron-regulated promoter sequences similar to that of irgA. Such promoter sequences are well-known to those of ordinary skill, or can be readily determined from current information regarding iron-regulated promoters. Construction of such promoter sequences adjacent to a given heterologous antigen-encoding sequence, and insertion of the resulting construct into a *V. cholerae* genome, is readily accomplished by one of ordinary skill; the ability of such a promoter to function as predicted can then be tested in low- and high-iron conditions as described below, without undue experimentation.

Also within the invention is a *V. cholerae* cell, or a homogeneous population of such cells, which contains the genetically engineered chromosome described above. Such cells can be said to define a vaccine strain useful, when combined with a pharmaceutically acceptable diluent suitable for oral administration, as a live-cell vaccine. Administration of such a vaccine to an animal (e.g., a human or other mammal) will provoke immunity not only to *V. cholerae*, but also to an antigen derived from a second organism; it thus serves as a bivalent vaccine. An example of such a vaccine utilizes a genetically engineered *V. cholerae* strain in which the ctxA and irgA coding sequences are largely deleted and a sequence encoding Shiga-like toxin B subunit is functionally linked to the irgA promoter. This strain is described in detail below. Of course, the bacterial strain of the invention could be engineered to encode several heterologous antigens, each linked to an identical or different iron-regulated promoter, to produce a multivalent vaccine effective for simultaneously inducing immunity against a number of infectious diseases.

Other features and advantages will be apparent from the detailed description provided below, and from the claims.

BRIEF DESCRIPTION OF THE DRAWINGS

FIGS. 2A–D is a set of Southern blots illustrating hybridization of chromosomal DNA from wild-type and mutant V. cholerae strains, digested with HindIII, separated by agarose electrophoresis and probed as follows: (A) SmaI - HincII fragment (region deleted in vaccine strains); (B) HincII - HincII fragment (downstream probe); (C) HindIII - SmaI fragment (upstream probe); (D) EcoRV - HindIII fragment from pSBC52 (slt-IB subunit probe). Lanes: 1, 0395-N1; 2, SBC20; 3, BO14-1; 4, BO24-1; 5, VAC1; 6, VAC2; 7, 0395-N1. The genomic location of the fragments used as probes is indicated in FIG. 1. The numbers to the left of the blot indicate the sizes (in kbp) of DNA standards.

FIG. 4 is a schematic diagram of the construction of the pSBC52 plasmid utilized in these experiments. pSBC32 (Calderwood et al., Infect. Immun. 58:2977–2982, 1990) was subjected to PCR using primer No. 1: 5'-CCGAATTCTCTAGAGATATCGTGTGGAATTGTGA GCGGATAA-3' (SEQ ID NO: 11), which introduces restriction sites for EcoRI, XbaI, and EcoRV, and primer No. 2: 5'-CCAAGCTTCTGCAGCCCGGGATTTAACATTTATG AATCTCCGCCT-3' (SEQ ID NO: 12), which introduces restriction sites for HindIII, PstI, and SmaI. The PCR product was then digested with EcoRI and HindIII, and cloned into EcoRI/HindIII-digested pUC19, to produce pSBC52.

FIG. 5 shows the nucleotide sequence of a portion of the irgA cDNA (SEQ ID NO: 1), including the promoter sequence. A 19-bp interrupted dyad symmetric element homologous to the Fur box of E. coli is indicated by inverted horizontal arrows below the sequence. Vertical lines mark the margins of what is believed to be regions important for irgA promoter function.

DETAILED DESCRIPTION

In the experiments described below, the non-toxic B subunit of Shiga toxin was used as a model heterologous antigen, because of the easily available assays for this protein (Donohue-Rolfe et al., J. Clin. Microbiol. 24:65–68, 1986), as well as the possible role that antibodies against the B subunit play in protecting against severe Shigellosis and hemolytic uremic syndrome. Shiga toxin is a heterodimeric protein consisting of one A subunit (MW 32 kDa) and five B subunits (MW 7.7 kDa) (Seidah et al., J. Biol. Chem. 261:13928–13931, 1986); the B subunit of Shiga toxin is identical in amino acid sequence to the B subunit of Shiga-like toxin I produced by enterohemorrhagic strains of E. coli (Calderwood et al., Proc. Natl. Acad. Sci. USA 84:4364–4368, 1987). This identical protein product is referred to as StxB throughout this study. Immune response to Shiga toxin is primarily directed against the B subunit, and antibodies directed against this subunit, or against synthetic peptides from regions of the subunit, provide protective immunity against holotoxin (Donohue-Rolfe et al., J. Exp. Med. 160:1767–1781, 1984; Harari et al. Infect. Immun. 56:1618–1624, 1988; Harari et al., Mol. Immunol. 27:613–621, 1990; Boyd et al., Infect. Immun. 59:750–757, 1991).

Described below are the insertion of a promoterless gene for the Shiga-like toxin I B subunit (slt-IB) into an irgA deletion, and the introduction of this construct into the chromosome of the V. cholerae ctxA deletion strain 0395-N1, thus producing a live, attenuated vaccine strain of V. cholerae that contains StxB under the transcriptional control of the iron-regulated irgA promoter.

MATERIALS AND METHODS

Bacterial Strains and Plasmids

Figure 1A:
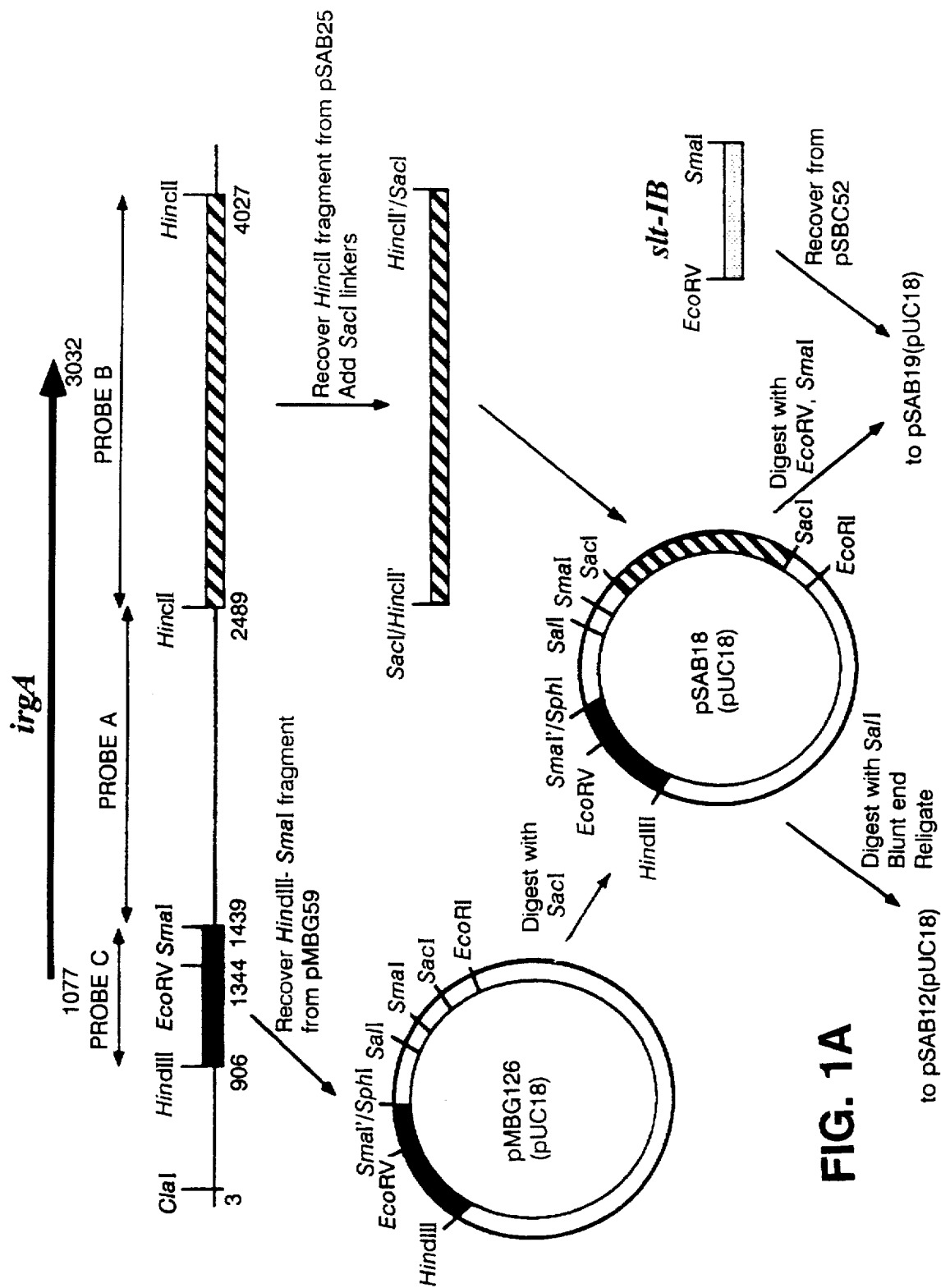
FIG. 1 is a schematic diagram illustrating the construction of plasmids used in this study. A partial restriction map of 0395 chromosomal DNA is shown with relevant restriction enzyme sites, using base-pair numbering as in Goldberg et al., Mol. Microbiol. 6:2407–2418, 1992; and Goldberg et al., Proc. Natl. Acad. Sci. USA 88:1125–1129, 1991. The location of irgA, the location of fragments cloned in the construction of vaccine strains and the locations of fragments used as probes in Southern blot analysis are indicated. The upstream irgA fragment is indicated by a solid bar; the downstream irgA fragment by a hatched bar; and the slt-IB subunit fragment by a stippled bar. Plasmids and chromosomal fragments are not drawn to scale.
Figure 1B:
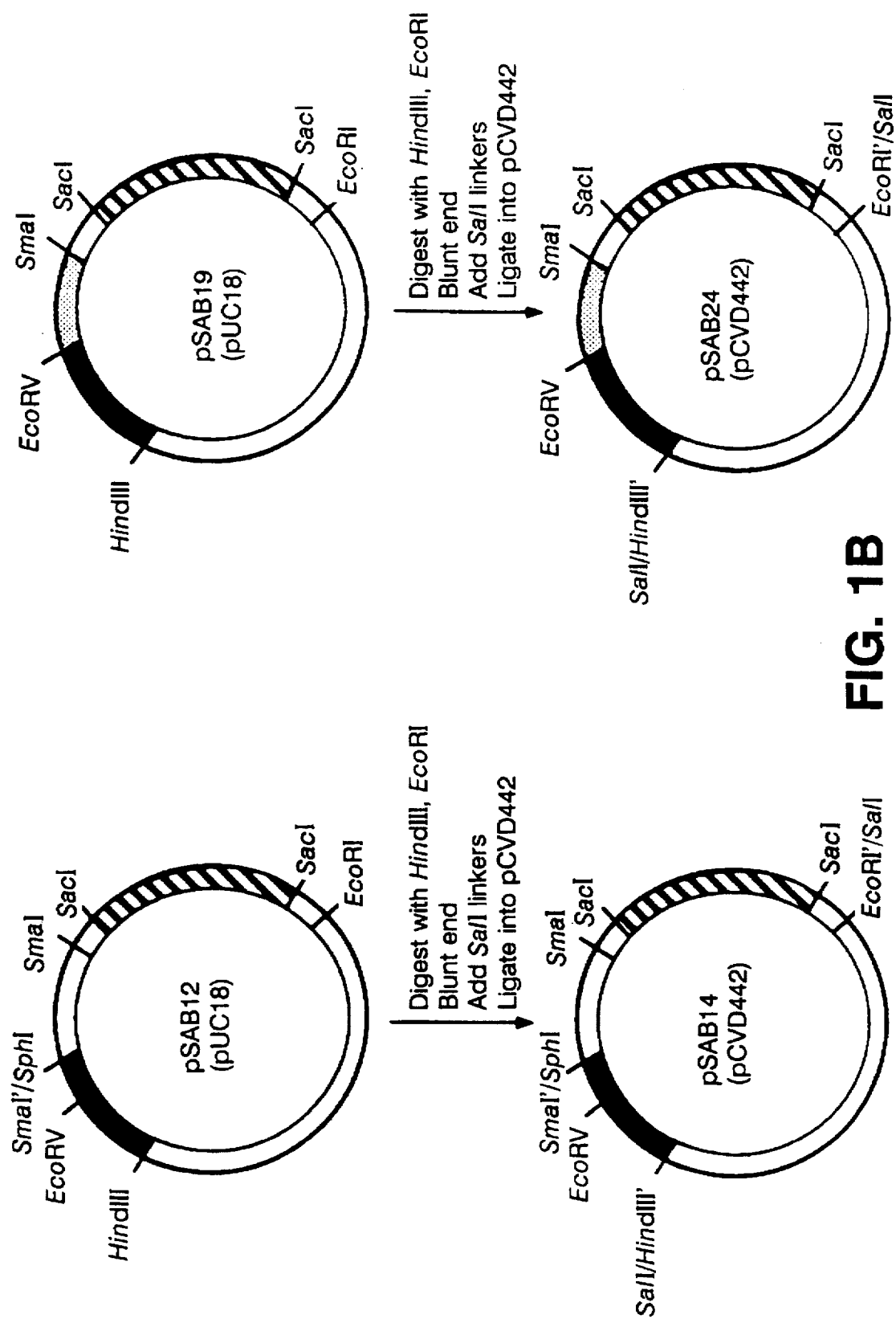

The bacterial strains and plasmids used in this study are described in Table 1, with the exception of plasmids pMBG126, pSAB18, pSAB12, pSAB19, pSAB14, and pSAB24, which are described in detail below and are depicted in FIG. 1; and plasmid pSBC52, which is described in the description of FIG. 4 provided above. Standard plasmid cloning vectors pUC18, pUC19, and pBR322 are commercially available (e.g., Pharmacia).

Media

All strains were maintained at −70° C. in Luria broth (LB) media (Sambrook et al., A Laboratory Manual, 2nd ed. Cold Spring Harbor Laboratory Press, Cold Spring Harbor, N.Y., 1989), containing 15% glycerol. LB media, with or without the addition of the iron chelator 2,2-dipyridyl (final concentration, 0.2 mM), was used for growth in low- and high-iron conditions, respectively. Ampicillin (100 µg/ml), kanamycin (45 µg/ml), and streptomycin (100 µg/ml) were added as appropriate.

Genetic Methods

Isolation of plasmid and bacterial chromosomal DNA, restriction enzyme digests, agarose gel electrophoresis, and Southern hybridization of DNA separated by electrophoresis were performed according to standard molecular biologic techniques (Sambrook, supra). GeneScreen Plus hybridization transfer membranes (DuPont Biotechnology Systems, NEN Research Products, Boston, Mass.) were used according to the manufacturer's protocols for Southern hybridization. DNA sequencing was performed using the Sequenase DNA Sequencing Kit (United States Biochemical Corporation, Cleveland, Ohio).

Plasmids were transformed into E. coli strains by standard techniques, or were electroplated into V. cholerae using a Gene Pulser (Bio-Rad Laboratories, Richmond, Calif.), following the manufacturer's protocol, and modified for electroporation into V. cholerae as previously described (Goldberg et al., Proc. Natl. Acad. Sci. USA 88:1125–1129, 1991). Electroporation conditions were 2,500 V at 25-µF capacitance, producing time constants of 4.7–4.9 ms.

DNA restriction endonucleases, $T_4$ DNA ligase, calf intestinal alkaline phosphatase, and the Klenow fragment of DNA polymerase I were used according to the manufacturers' specifications. Restriction enzyme-digested chromosomal and plasmid DNA fragments were separated on 1% agarose gels; required fragments were cut from the gel under ultraviolet illumination and purified by electroelution (Sambrook et al. 1989, supra). DNA fragments used as probes were radiolabeled with $\alpha$-$^{32}$P-dCTP using a random priming labeling kit (Prime Time "C" Oligonucleotide Labeling Biosystem, International Biotechnologies, Inc., New Haven, Conn.).

Construction of Plasmids

DNA was recovered upstream and at the 5' terminus of irgA as a HindIII-SmaI fragment from pMBG59, which contains the irgA promoter (irgP) (Goldberg et al., J. Bacteriol. 172:6863–6870, 1990) (FIG. 1). This fragment was cloned into the HindIII and SphI sites of pUC18 to yield plasmid pMBG126; the SphI site of pUC18 had first been made blunt-ended by treatment with mung bean nuclease. DNA sequence analysis of pMBG126 revealed that the SphI site was unexpectedly preserved at the junction with SmaI; the sequence was otherwise as predicted. DNA was then recovered at the 3' terminus and downstream of irgA as a 1.5 kilobase-pair (kbp) HincII fragment from plasmid pSAB25. SacI linkers were added to this fragment and it was ligated into the unique SacI site of pMBG126, in the same orientation as the upstream irgA fragment, to yield plasmid pSAB18. The internal SalI site in the pUC polylinker of pSAB18 was removed by digesting with SalI, treating with the Klenow fragment of DNA polymerase I, and religating the blunt ends, to create pSAB12. A DNA segment encoding the promoterless B subunit of Shiga-like toxin I (slt-IB) was recovered as an EcoRV-SmaI fragment from plasmid pSBC52. This fragment was introduced into the unique EcoRV and SmaI sites of pSAB18, such that slt-IB was under the transcriptional control of irgP on the upstream irgA fragment, yielding plasmid pSAB19. The construction of plasmids pMBG126, pSAB18, pSAB12, and pSAB19 was verified by restriction enzyme digestion and double-stranded DNA sequencing.

The desired fragments were then introduced into the suicide vector pCVD442 as follows. pSAB12 and pSAB19 were digested with HindIII and EcoRI and the DNA fragment containing either the irgA deletion (from pSAB12) or the irgA deletion-slt-IB-substitution (from pSAB19) were made blunt-ended by the Klenow fragment of DNA polymerase I. Following ligation to SalI linkers, the fragments were ligated into the unique SalI site of pCVD442, yielding plasmids pSAB14 and pSAB24 respectively, and propagated in the permissive strain SM10 λ pir. Plasmid pCVD442 is a recently described suicide vector containing the pir-dependent R6K replicon, ampicillin resistance, and the sacB gene from *Bacillus subtilis* (Donnenberg et al., Infect. Immun. 59:4310–4317, 1991).

Construction of VAC1 and VAC2

*V. cholerae* strain SBC20 is an irgA::TnphoA derivative of 0395-N1 (Pearson et al., Res. Microbiol. 141:893–899, 1990). The kanamycin resistance marker in TnphoA allowed screening of mutants for deletion of irgA (and hence TnphoA) by assessing susceptibility to kanamycin. The irgA allele of SBC20 was replaced with either the previously constructed irgA deletion, or the irgA deletion containing slt-IB, as follows. Plasmids pSAB14 and pSAB24 were electroporated into SBC20, with selection for ampicillin and streptomycin resistance. Doubly-resistant colonies contained the respective plasmids integrated into the chromosome by homologous recombination involving either the upstream or downstream fragments of irgA on pSAB14 or pSAB24, with creation of a merodiploid state. One such colony from the integration of pSAB14 into the chromosome of SBC20 was selected and named BO14-1; one from the integration of pSAB24 into the chromosome of SBC20 was named BO24-1. BO14-1 and BO24-1 were grown overnight in LB media without ampicillin selection, then plated on LB media with 10% sucrose but without NaCl, and grown at 30° C. for 30 hours, thereby selecting for clones that had deleted the integrated sacB gene (Blomfield et al., Mol. Microbiol. 5: 1447–1457, 1991). Sucrose-resistant colonies that are ampicillin susceptible but kanamycin resistant have re-excised the plasmid (yielding the parent SBC20, which contains the kanamycin resistance marker in TnphoA); those that are both ampicillin and kanamycin susceptible have resolved the merodiploid state to replace the irgA locus in SBC20 with either the irgA deletion from pSAB14 or the irgA deletion-slt-IB fragment from pSAB24. Approximately 10% of sucrose-resistant colonies that were ampicillin-susceptible were also kanamycin-susceptible. One of these colonies which had replaced the irgA::TnphoA locus with the irgA deletion was further purified and named VAC1; one which had replaced the irgA::TnphoA locus with irgA::irgP-slt-IB was named VAC2. Confirmation of the proper constructions in VAC1 and VAC2 was obtained by Southern hybridization of restriction enzyme-digested chromosomal DNA that was probed with several different DNA fragments to verify the expected deletion in irgA, as well as the introduction of the slt-IB within the deleted irgA segment.

Preparation of Outer-Membrane Proteins, Whole Cell Proteins, and Periplasmic Extracts Enriched outer membrane proteins were prepared from strains following growth in low- and high-iron media as previously described (Goldberg, Infect. Immun. 58:55–60, 1990). Proteins were separated by electrophoresis on a sodium dodecyl sulfate/10% polyacrylamide (SDS-PAGE) gel and visualized by staining with Coomassie brilliant blue. Whole cell proteins and periplasmic extracts were prepared from exponentially growing cells as previously described (Hovde et al., Proc. Natl. Acad. Sci. USA 85:2568–2572, 1988).

Immunodetection of StxB Production

Whole cell proteins and periplasmic extracts were separated on a SDS-15% PAGE gel as described above, then transferred to a NitroBind Transfer Membrane (Micron Separations Inc., Westboro, Mass.) with a semidry blotting apparatus (Hoefer Scientific Instruments, San Francisco, Calif.). Immunoreactive proteins were visualized after sequential incubation with polyclonal rabbit anti-Shiga toxin antiserum and goat anti-rabbit IgG-conjugated alkaline phosphatase (Sigma Chemical Co., St. Louis, Mo.), followed by staining for phosphatase activity as described previously (Hovde, supra). The amount of StxB present in periplasmic extracts or culture supernatants was quantitated with an enzyme-linked immunosorbent assay (ELISA) developed for the detection of Shiga toxin and modified for detection of purified StxB (Donohue-Rolfe et al., J. Clin. Microbiol. 24:65–68, 1986; Calderwood et al., Infect. Immun. 58:2977–2982, 1990).

HeLa Cell Cytotoxicity

The cytotoxicity of periplasmic extracts or culture supernatants for HeLa cells was assayed in a quantitative cytotoxicity assay by determining the extent of HeLa cell detachment from microtiter plates (Gentry et al., J. Clin. Microbiol. 12:361–366, 1980). HeLa cells were grown at 37° C. in a 5% $CO_2$ atmosphere in McCoy 5a (modified) medium containing 10% fetal calf serum and 100 μg of penicillin and streptomycin per ml. Freshly trypsinized cells were suspended in 0.1 ml of growth medium and allowed to attach to the wells of microtiter plates overnight. Serial dilutions of samples were added and the plates were again incubated overnight. The cells were fixed and then stained with crystal violet in a 5% ethanol - 2% formaldehyde solution. Stained cell monolayers were dissolved in ethanol and the $A_{595}$ read with a microtiter plate colorimeter.

Evaluation of Virulence of Vaccine Strains

50% lethal dose ($LD_{50}$) assays were performed by oral inoculation of 3- to 4-day old CD1 suckling mice with either the parent V. cholerae strain 0395, an irgA mutant strain MBG40 (Goldberg et al., Infect. Immun. 58:55–60, 1990), the ctxA mutant strain 0395-N1, or VAC2. Cholera strains were grown overnight in LB medium at 30° C., pelleted, and resuspended in 0.5M $NaHCO_3$ (pH 8.5). Mice were orally inoculated with serial dilutions of organisms, then kept at 30° C. Four or more mice were used per dose of bacteria. Survivial was determined at 40 h (Taylor et al., Proc. Natl. Acad. Sci. USA 84:2833–2837, 1987).

RESULTS

Figures 2C, 2D:
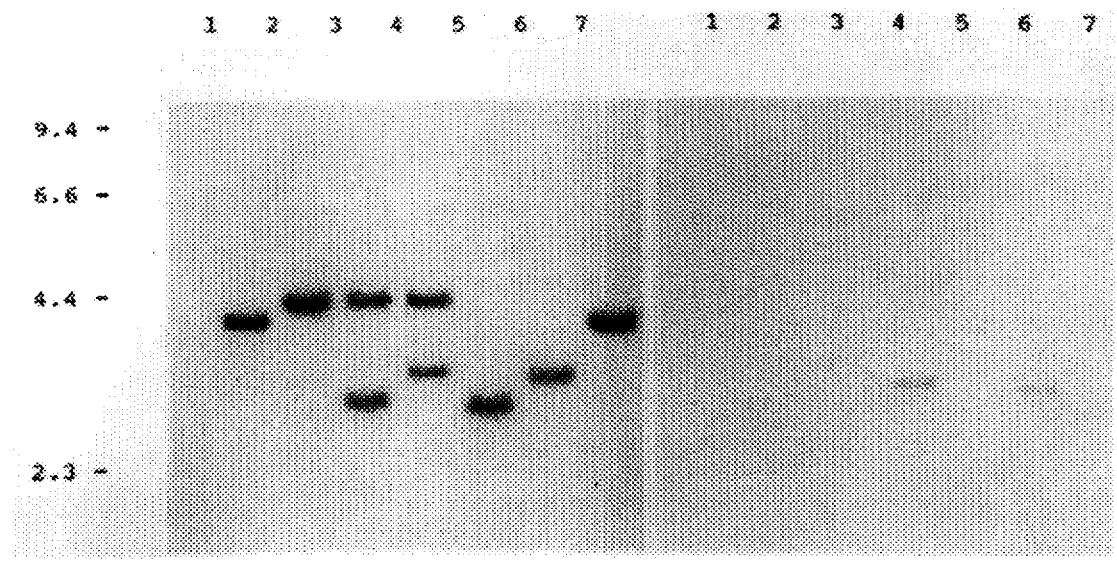
Figure 3:
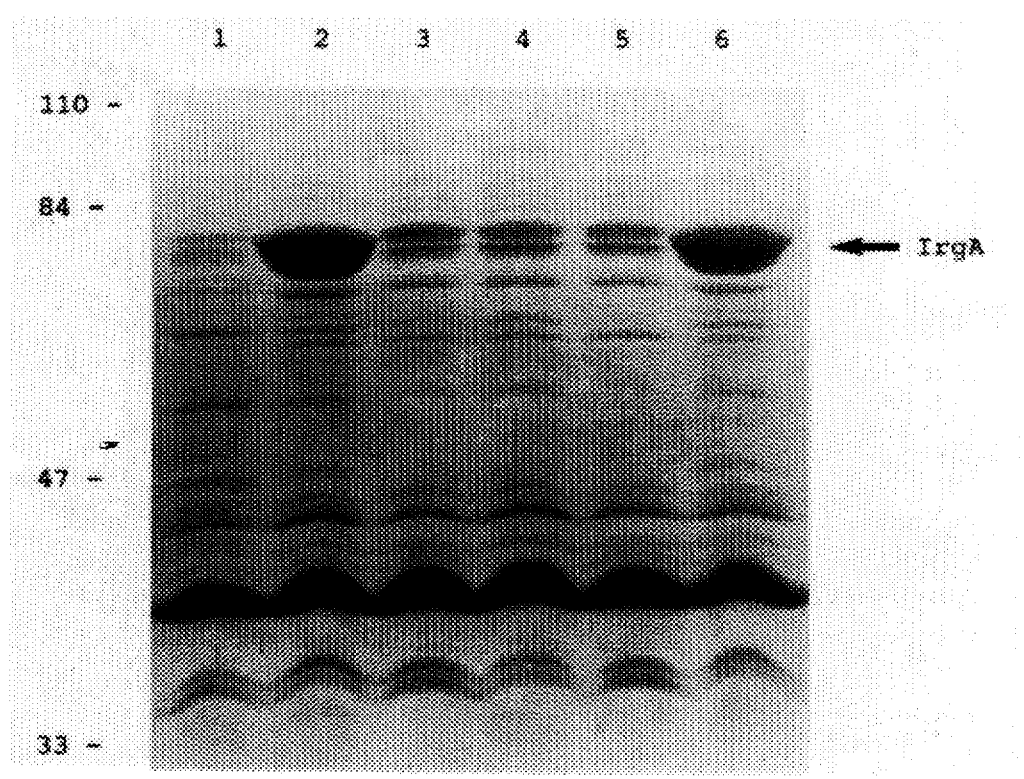
FIG. 3 is a photograph of an SDS-PAGE analysis of the outer membrane proteins expressed by certain V. cholerae strains when grown in high- or low-iron medium. Lanes: 1, 0395-N1 grown in high-iron medium; 2, 0395-N1 grown in low-iron medium; 3, SBC20 grown in low-iron medium; 4, VAC1 grown in low-iron medium; 5, VAC2 grown in low-iron medium; 6, 0395-N1 grown in low-iron medium. The numbers to the left of the gel indicate the molecular masses (in kDa) of the protein standards.

Confirmation of Vaccine Strain Construction (i) Southern hybridization analysis. To confirm the construction of the vaccine strains, chromosomal DNA was purified from V. cholerae parent strains 0395-N1 and SBC20, the merodiploid strains BO14-1 and BO24-1, and the vaccine strains VAC1 and VAC2. The chromosomal DNAs were digested with HindIII, separated on agarose gels, and transferred to membranes for Southern hybridizations. The Southern hybridizations of these digests, probed with four different fragment probes, are shown in FIG. 2. The location of the fragment probes within the irgA gene is shown in FIG. 1. The presence and size of the recognized fragments is consistent with the constructions depicted in FIG. 1, confirming the deletion of irgA in VAC1 and the deletion-replacement of the irgA locus with irgA::irgP-sltIB in VAC2.

ii. Outer membrane protein analysis. Outer membrane proteins were prepared from strain 0395-N1 grown in low- and high-iron media and from strains SBC20, VAC1 and VAC2 following growth in low-iron media, then separated by electrophoresis on a SDS-PAGE gel (FIG. 3). IrgA, the 77 kilodalton (kDa) major iron-regulated outer membrane protein (Goldberg et al., Infect. Immun. 58:55–60, 1990), is present in 0395-N1 grown in low iron but is absent in SBC20 (an irgA mutant) and the vaccine strains, confirming the deletion of irgA in VAC1 and VAC2.

Iron-Regulated Expression of the Shiga Toxin B Subunit in VAC2

(i) Western blot analysis of StxB production in VAC2. Western blot analysis of whole cell proteins and periplasmic extracts of VAC2 grown in high- and low-iron media demonstrated the production of a 7.7 kDa protein recognized by polyclonal rabbit anti-Shiga toxin antiserum in both whole cell proteins and periplasmic extracts prepared from VAC2 grown in low-iron media; no such protein was recognized in proteins prepared from the vaccine strain grown in high-iron media, demonstrating that the production of StxB is tightly iron-regulated (data not shown).

(ii) Quantitation of StxB production from irgP-slt-IB in plasmid pSAB19 and VAC2. To verify iron-regulated production of StxB by irgP-slt-IB in plasmid pSAB19, and compare it with StxB production by VAC2, we first had to return pSAB19 to the V. cholerae background because irgP is not active in E. coli (Goldberg et al., Proc. Natl. Acad. Sci. USA 88:1125–1129, 1991). The production of StxB by strains 0395-N1(pSAB19) and VAC2 was quantitated using a sandwich ELISA, with a monoclonal antibody specific for StxB as the capture molecule. Purified StxB, in measured amounts, was used as the standard. As shown in Table 2, both 0395-N1(pSAB19) and VAC2 express StxB in a tightly iron-regulated fashion, as expected, and produce five times the amount of B subunit made by the reference strain, Shigella dysenteriae 60R, under low-iron conditions.

Virulence of Vaccine Strains (i) Cytotoxicity to HeLa cells. The cytotoxicity of periplasmic extracts or culture supernatants of strains 0395-N1 (pSAB19) and VAC2, grown in low-iron media, was assayed as described (Gentry et al., J. Clin. Microbiol. 12:361–366, 1980), and compared to the S. dysenteriae strain 60R. Neither 0395-N1(pSAB19) or VAC2 had detectable cytotoxicity in periplasmic extracts or supernatants, in contrast to periplasmic extracts of S. dysenteriae 60R, which were cytotoxic to at least a $10^5$-fold dilution (data not shown).

(ii) $LD_{50}$ assays. The results of $LD_{50}$ assays for the wild-type V. cholerae strain 0395, ctxA mutant strain 0395-N1, irgA mutant strain MBG40, and vaccine strain VAC2 in the suckling mouse model are shown in Table 3. V. cholerae strain MBG40, an irgA::TnphoA mutant of strain 0395, had an $LD_{50}$ in suckling mice that was 2 orders of magnitude higher than that for the parental strain 0395, as previously demonstrated (Goldberg et al., Infect. Immun. 58:55–60, 1990). Strain 0395-N1, deleted for the A subunit of cholera toxin, was avirulent at an inoculum of $2 \times 10^9$ organisms in this model. The vaccine strain VAC2, despite expressing StxB at high level, remains avirulent in this model at an inoculum of $2 \times 10^9$ organisms, similar to its parent strain 0395-N1.

USE

The V. cholerae strains of the invention are useful as bivalent vaccines capable of inducing immunity to V. cholerae and to an antigen derived from a second infectious organism. Because the strains are attenuated (i.e., do not induce a significant toxic reaction in the vaccinee), they can be used as live-cell vaccines, permitting effective immunity to result from administration of a single dose of the vaccine. An effective oral dose of the vaccine would contain approximately $10^6$ to $10^8$ bacteria in a volume of approximately 150 ml liquid. The diluent used would typically be water or an aqueous solution, such as 2 grams of sodium bicarbonate dissolved in 150 ml distilled water, which may be ingested by the vaccinee at one sitting, either all at once or over any convenient period of time.

Other Embodiments

Other embodiments are within the claims set forth below. For example, the host bacterium (the bacterium the chromosome of which is engineered to encode a heterologous antigen) can be E. coli or any other enteric bacterium, including Salmonella, Shigella, Yersenia, Citrobacter, Enterobacter, Klebsiella, Morganella, Proteus, Providencia, Serratia, Plesiomonas, and Aeromonas, all of which are known or believed to have iron-regulated promoters similar to the Fur-binding promoters of *E. coli*, and which may have other iron-regulated promoters analogous to that of irgA. Also potentially useful would be a bacille Calmette-Guerin (BCG) vaccine strain engineered to encode a heterologous antigen linked to an iron-regulated promoter. The promoter used can be native to the species of the host bacterium, or can be a heterologous promoter (i.e., from a species other than that of the host bacterium) engineered into the host bacterium along with the heterologous antigen coding sequence, using standard genetic engineering techniques. Multiple heterologous antigen coding sequences linked to the same or different iron-regulated promoter sequences can be inserted into a given chromosome, using techniques analogous to those set forth above, to produce a multivalent vaccine strain.

Those who practice in the field of prokaryotic gene expression will realize that, while naturally-occurring promoter sequences are preferred, synthetic sequences such as a consensus Fur-binding sequence or a hybrid of two or more Fur-binding sequences would also be expected to be useful in the chromosomes of the invention. Alteration, addition or deletion of one or a few nucleotides within a naturally-occurring promoter sequence such as the irgA promoter would generally not affect its usefulness. The invention therefore encompasses iron regulated promoters having such inconsequential changes.

TABLE 1

Bacterial strains and plasmids used in this study

| Strain or plasmid | Relevant genotype or phenotype | Ref. or source |
|---|---|---|
| *V. cholerae* strains | | |
| 0395 | $Sm^r$ | 1 |
| 0395-N1 | 0395 ctxA, $Sm^r$ | 1 |
| SBC20 | 0395-N1 irgA::TnphoA, $Sm^r$, $Km^r$ | 2 |
| MBG40 | 0395 irgA::TnphoA, $Sm^r$, $Km^r$ | 3 |
| BO14-1 | SBC20 with PSAB14 integrated into irgA, $Sm^r$, $Km^r$, $Ap^r$ | 4 |
| BO24-1 | SBC20 with pSAB24 integrated into irgA, $Sm^r$, $Km^r$, $Ap^r$ | 4 |
| VAC1 | 0395-N1 ΔirgA, $Sm^r$ | 4 |
| VAC2 | 0395-N1 ΔirgA::irgP-slt-IB, $Sm^r$ | 4 |
| *E. coli* strains | | |
| SM10 λ pir | thi thr leu tonA lacY supE recA::RP4-2-Tc::Mu λ pirR6K, $Km^r$ | 5 |
| Plasmids | | |
| pMBG59 | pBR322 with 4.7-kbp of *V. cholerae* MBG40 chromosome, containing DNA upstream and at the 5' terminus of irgA, as well as the irgA::TnphoA fusion joint from this strain. | 6 |
| pSAB25 | 3.0 kbp SmaI - MluI fragment of *V. cholerae* 0395 chromosome, containing DNA at the 3' terminus and downstream of irgA, made blunt- | 4 |

TABLE 1-continued

Bacterial strains and plasmids used in this study

| Strain or plasmid | Relevant genotype or phenotype | Ref. or source |
|---|---|---|
| | ended at the MluI site and ligated into SmaI-digested pUC19. | |
| pSBC52 | pUC19 with a promoterless gene for the B subunit of SLT-I (identical to StxB) cloned between the EcoRI and HindIII sites. | 4 |
| pCVD442 | Suicide vector composed of the mob, ori, and bla regions from pGP704 and the sacB gene of *Bacillus subtilis*. | 7 |

$Ap^r$, ampicillin resistance; $Km^r$, kanamycin resistance; $Sm^r$, streptomycin resistance.

Ref. or source:
1. Mekalanos et al., Nature 306:551–557, 1983.
2. Pearson et al., Res. Microbiol. 141:893–899, 1990.
3. Goldberg et al., Infect. Immun. 58:55–60, 1990.
4. This study.
5. Miller et al., J. Bacteriol. 170:2575–2583, 1988.
6. Goldberg et al., J. acteriol. 172:6863–6870, 1990.
7. Donnenberg and Kaper, Infect. Immun. 59:4310–4317, 1991.

TABLE 2

Production of Shiga toxin B subunit by various strains following growth in high- and-low iron conditions

| | Periplasmic extract[a] | | Supernatant[a] | |
|---|---|---|---|---|
| Strain | High-iron | Low-iron | High-iron | Low-iron |
| 0395-N1 | —[b] | — | — | — |
| 0395-N1 (pSAB19) | 15.5 | 3,620 | 0.16 | 3.5 |
| VAC2 | 0.87 | 4,130 | — | 0.73 |
| *S. dysenteriae* 60R | 238 | 674 | 0.8 | 16.4 |

[a] ng/50 $OD_{600}$ of original culture
[b] <0.1 ng

TABLE 3

Virulence assays of wild-type and mutant strains of *Vibrio cholerae* in suckling mice

| Strain | $LD_{50}$ (no. of bacteria) |
|---|---|
| 0395 | $1 \times 10^5$ |
| MBG40 | $1 \times 10^7$ |
| 0395-N1 | $>2 \times 10^9$ |
| VAC2 | $>2 \times 10^9$ |

We claim:

1. A process for inducing in an animal an immune response against a heterologous antigen, the sequence of which does not comprise the sequence of a full length polypeptide expressed by wildtype *V. cholerae*, comprising administering to said animal recombinant *V. cholerae* containing DNA encoding said heterologous antigen, said heterologous antigen being expressed from said DNA in said animal, provided that said heterologous antigen (a) comprises an antigenic part, or all, of a protein that is naturally expressed by an infectious organism other than wildtype *V. cholerae*, and (b) induces an immune response in an animal.

2. The process of claim 1, wherein said DNA encoding said heterologous antigen is functionally linked to a promoter of a naturally-occurring *V. cholerae* gene.

3. The process of claim 1, wherein said heterologous antigen is a nontoxic polypeptide.

4. The process of claim 1, wherein said heterologous antigen is a portion or all of a protein naturally expressed by an infectious organism.

5. The process of claim 1, wherein said infectious organism is a bacterium.

6. The process of claim 1, wherein said heterologous antigen comprises an immunogenic, nontoxic subunit or fragment of a bacterial toxin.

7. The process of claim 6, wherein said toxin is Shiga toxin, diphtheria toxin, Pseudomonas exotoxin A, cholera toxin, pertussis toxin, tetanus toxin, anthrax toxin, *E. coli* heat-labile toxin (LT), *E. coli* heat-stable toxin (ST), or *E. coli* Shiga-like toxin.

8. The process of claim 5, wherein said protein is an OSP (Outer Surface Protein) of *Borrelia burgdorferi*.

9. The process of claim 1, wherein said infectious organism is a virus and said protein is an immunogenic portion of a viral capsid.

10. The process of claim 9, wherein said virus is a human immunodeficiency virus (HIV), one of the Herpes viruses, an influenza virus, a poliomyelitis virus, a measles virus, a mumps virus, or a rubella virus.

11. The process of claim 1, wherein said infectious organism is a eukaryotic parasite.

12. The process of claim 11, wherein said parasite is the causative agent for malaria, pneumocystis pneumonia, or toxoplasmosis.

13. The process of claim 12, wherein said protein is a malarial circumsporozoite protein.

14. The process of claim 1, wherein the chromosome of said recombinant *V. cholerae* does not encode a biologically active cholera toxin A subunit.

15. The process of claim 2, wherein said promoter is an iron-regulated promoter.

16. The process of claim 2, wherein said naturally-occurring *V. cholerae* gene is irgA.

17. A composition comprising (A) recombinant *V. cholerae* containing DNA encoding a heterologous antigen, the sequence of which does not comprise the sequence of a full length polypeptide expressed by wildtype *V. cholerae*, and (B) a pharmaceutically acceptable diluent, provided that said heterologous antigen (1) comprises an antigenic part, or all, of a protein that is naturally expressed by an infectious organism other than wildtype *V. cholerae*, and (2) induces an immune response in an animal.

18. The composition of claim 17, wherein said DNA is functionally linked to a naturally-occurring *V. cholerae* promoter.

19. The composition of claim 18, wherein said promoter is the promoter of a naturally-occurring gene encoding a *V. cholerae* virulence factor that is nonessential for growth of said cell, the coding sequence encoding said virulence factor being mutated or deleted so that said *V. cholerae* cannot express a biologically active form of said virulence factor.

20. The composition of claim 17, wherein said heterologous antigen comprises an antigenic portion of a protein naturally expressed by a first infectious organism and an antigenic portion of a protein naturally expressed by a second infectious organism.

21. The composition of claim 17, wherein said infectious organism is a bacterium.

22. The composition of claim 17, wherein said heterologous antigen comprises an immunogenic, nontoxic subunit or fragment of a bacterial toxin.

23. The composition of claim 22, wherein said toxin is Shiga toxin, diphtheria toxin, Pseudomonas exotoxin A, cholera toxin, pertussis toxin, tetanus toxin, anthrax toxin, *E. coli* LT, *E. coli* ST, or *E. coli* Shiga-like toxin.

24. The composition of claim 17, wherein said infectious organism is a virus and said protein is a viral protein.

25. The composition of claim 24, wherein said virus is a human immunodeficiency virus (HIV), one of the Herpes viruses, an influenza virus, a poliomyelitis virus, a measles virus, a mumps virus, or a rubella virus.

26. The composition of claim 17, wherein said infectious organism is a eukaryotic parasite.

27. The composition of claim 26, wherein said parasite is the causative agent for malaria, pneumocystic pneumonia, or toxoplasmosis.

28. The composition of claim 17, wherein said *V. cholerae* does not express biologically active cholera toxin A subunit.

29. The composition of claim 17, wherein said *V. cholerae* is a live cell.

30. The composition of claim 17, wherein the chromosome of said *V. cholerae* does not encode biologically active IrgA.

31. The composition of claim 17, wherein said protein is Shiga-like toxin B subunit.

32. A method of inducing an immune response in an animal comprising orally administering to said animal the composition of claim 17.

33. The method of claim 32, wherein said animal is a human.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 1535
        ( B ) TYPE: nucleic acid
        ( C ) STRANDEDNESS: both
        ( D ) TOPOLOGY: linear ( x i ) SEQUENCE DESCRIPTION: SEQ ID NO: 1:

```
ATCGATGATA  AAAAATCCCG  CTGCGGCGGG  ATTTTTTATT  GCCACTCATC  GGGCCTTGCT     60

TGGCGGAGCG  CATCAATAAA  TAGGCGCAGC  CGAAGTGGGT  GACGACCGAG  CGGATAGAAG    120

CAGTTGATTT  CTGTTGGCTG  TGATTGCCAT  CCGTTGACGC  AAGGAATGAG  GCTGCCCGGA    180

TGCGCCGTTT  CAAAACCATT  GGCAAACCAA  GTGGGAAGCA  AACCAATACC  ACGACCTTTA    240

GCAATCGCAT  CGGCTTGCAT  GGCAAGATTA  TCGCTTTGTA  AACGACTCTC  TAGTGCTGGC    300

AGTGAATAAC  TGCCGAACTC  TGGATGGTGC  AGTTCAAGCT  CCGCGCGCCG  ACAAGCAATA    360

AAATCAATCC  ATGGGTGATG  AATCAGCTCA  CGAGGATGGG  TCGGTTTATC  TCGATGGGCC    420

AAATATTTGG  GAGAGGCGTA  AGTGGCATAG  CGCCAATAGC  CTAAGCGTTC  TTTGCGATAA    480

CCCATGGGGG  CGGCGTGTTC  AATCCAAATG  ATCAAATCGG  GCTCAAACAC  CTCATCACTG    540

TGTTGAAACT  GGCTGAGTAG  ACGGATCTTC  AATGTCGAAT  GCTGCTGCAT  AAACTCATCC    600

AATACTTGGC  TGAGCCAGCC  GCGGATCAAA  TTGGGGTGTA  CCACCAGCGT  GAGTTCGCCA    660

GTCACTTGAT  TGTTCAATTC  TTGCAACGCT  TCCTGACTTT  TATTGGCCAG  TTCAAGTAGT    720

TGCTCCGAGT  AAACCGCAAA  CACTTCTCCT  GCTTTGGTGA  GCGTTAAGCG  GTTGCCTTGA    780

CGCATCAACA  AGCTTTGTCC  CAAGTCCTCT  TCAAGTTGCG  CCAAACGGCG  ACTCAGGGTG    840

GATTTAGGCT  GTTCAAGCGC  TTTGGCAGCG  GCAGTCAGGC  TCTTATGTTG  GCAAAGCGCA    900

TGGAAAGCTT  TTACGGCGCT  GAGATCTTGC  ATAGGTATTT  GACCCTTAAA  GAATAATTAC    960

CACAGACGTT  CCATATTTGG  ACCGAACTAT  TCCATGTGTC  GATCTATCTC  CAGTACAGAA   1020

TATATGAATA  ATCCGCTTCT  GAAATTAAGA  ATAATTATCA  TTTAAAGGAG  TGGTAA       1076
```

| | | | | | | |
|---|---|---|---|---|---|---|
| ATG TCC AGA TTC AAT CCA TCC CCC GTC AGT TTA TCT GTG ACA CTA GGC | | | | | | 1124 |
| Met Ser Arg Phe Asn Pro Ser Pro Val Ser Leu Ser Val Thr Leu Gly | | | | | | |
| 1       5             10            15 | | | | | | |
| TTA ATG TTT TCG GCT AGC GCT TTT GCT CAA GAC GCG ACG AAA ACG GAT | | | | | | 1172 |
| Leu Met Phe Ser Ala Ser Ala Phe Ala Gln Asp Ala Thr Lys Thr Asp | | | | | | |
| 20              25            30 | | | | | | |
| GAA ACC ATG GTG GTC ACT GCG GCG GGA TAC GCG CAA GTG ATT CAA AAT | | | | | | 1220 |
| Glu Thr Met Val Val Thr Ala Ala Gly Tyr Ala Gln Val Ile Gln Asn | | | | | | |
| 35            40            45 | | | | | | |
| GCA CCA GCC AGT ATC AGT GTG ATT TCA AGA GAA GAT CTG GAA TCT CGC | | | | | | 1268 |
| Ala Pro Ala Ser Ile Ser Val Ile Ser Arg Glu Asp Leu Glu Ser Arg | | | | | | |
| 50            55            60 | | | | | | |
| TAT TAC CGT GAT GTG ACC GAT GCG CTA AAA AGC GTA CCG GGT GTG ACA | | | | | | 1316 |
| Tyr Tyr Arg Asp Val Thr Asp Ala Leu Lys Ser Val Pro Gly Val Thr | | | | | | |
| 65            70            75            80 | | | | | | |
| GTC ACC GGA GGG GGC GAT ACT ACC GAT ATC AGC ATT CGT GGT ATG GGA | | | | | | 1364 |
| Val Thr Gly Gly Gly Asp Thr Thr Asp Ile Ser Ile Arg Gly Met Gly | | | | | | |
| 85            90            95 | | | | | | |
| TCA AAC TAT ACT CTT ATC TTG GTG GAT GGT AAG CGC CAA ACC TCA CGC | | | | | | 1412 |
| Ser Asn Tyr Thr Leu Ile Leu Val Asp Gly Lys Arg Gln Thr Ser Arg | | | | | | |
| 100           105           110 | | | | | | |
| CAG ACC CGT CCA AAC AGC GAT GGC CCG GGC ATT GAG CAA GGT TGG TTA | | | | | | 1460 |
| Gln Thr Arg Pro Asn Ser Asp Gly Pro Gly Ile Glu Gln Gly Trp Leu | | | | | | |
| 115           120           125 | | | | | | |
| CCG CCA CTG CAA GCG ATT GAA CGT ATC GAG GTG ATC CGT GGC CCG ATG | | | | | | 1508 |
| Pro Pro Leu Gln Ala Ile Glu Arg Ile Glu Val Ile Arg Gly Pro Met | | | | | | |

|  | 130 |  |  |  | 135 |  |  | 140 |  |
|---|---|---|---|---|---|---|---|---|---|
| TCT | ACG | CTG | TAC | GGC | TCG | GAT | GCT | GAC |  | 1535
| Ser | Thr | Leu | Tyr | Gly | Ser | Asp | Ala | Asp |  |
| 145 |  |  |  |  | 150 |  |  |  |  |

( 2 ) INFORMATION FOR SEQ ID NO: 2:

( i ) SEQUENCE CHARACTERISTICS:
        ( A ) LENGTH: 51
        ( B ) TYPE: nucleic acid
        ( C ) STRANDEDNESS: both
        ( D ) TOPOLOGY: linear ( x i ) SEQUENCE DESCRIPTION: SEQ ID NO: 2:

TCCATGTGTC GATCTATCTC CAGTACAGAA TATATGAATA ATCCGCTTCT G    51

( 2 ) INFORMATION FOR SEQ ID NO: 3:

( i ) SEQUENCE CHARACTERISTICS:
        ( A ) LENGTH: 120
        ( B ) TYPE: nucleic acid
        ( C ) STRANDEDNESS: both
        ( D ) TOPOLOGY: linear ( x i ) SEQUENCE DESCRIPTION: SEQ ID NO: 3:

AGATCTTGCA TAGGTATTTG ACCCTTAAAG AATAATTACC ACAGACGTTC CATATTTGGA    60

CCGAACTATT CCATGTGTCG ATCTATCTCC AGTACAGAAT ATGAATAA TCCGCTTCTG    120

( 2 ) INFORMATION FOR SEQ ID NO: 4:

( i ) SEQUENCE CHARACTERISTICS:
        ( A ) LENGTH: 158
        ( B ) TYPE: nucleic acid
        ( C ) STRANDEDNESS: both
        ( D ) TOPOLOGY: linear ( x i ) SEQUENCE DESCRIPTION: SEQ ID NO: 4:

AGATCTTGCA TAGGTATTTG ACCCTTAAAG AATAATTACC ACAGACGTTC CATATTTGGA    60

CCGAACTATT CCATGTGTCG ATCTATCTCC AGTACAGAAT ATGAATAA TCCGCTTCTG    120

AAATTAAGAA TAATTATCAT TTAAAGGAGT GGTAAATG    158

( 2 ) INFORMATION FOR SEQ ID NO: 5:

( i ) SEQUENCE CHARACTERISTICS:
        ( A ) LENGTH: 80
        ( B ) TYPE: nucleic acid
        ( C ) STRANDEDNESS: both
        ( D ) TOPOLOGY: linear ( x i ) SEQUENCE DESCRIPTION: SEQ ID NO: 5:

CGATCTATCT CCAGTACAGA ATATATGAAT AATCCGCTTC TGAAATTAAG AATAATTATC    60

ATTTAAAGGA GTGGTAAATG    80

( 2 ) INFORMATION FOR SEQ ID NO: 6:

( i ) SEQUENCE CHARACTERISTICS:
        ( A ) LENGTH: 137
        ( B ) TYPE: nucleic acid
        ( C ) STRANDEDNESS: both
        ( D ) TOPOLOGY: linear ( x i ) SEQUENCE DESCRIPTION: SEQ ID NO: 6:

AAGCTTTTAC GGCGCTGAGA TCTTGCATAG GTATTTGACC CTTAAAGAAT AATTACCACA    60

GACGTTCCAT ATTTGGACCG AACTATTCCA TGTGTCGATC TATCTCCAGT ACAGAATATA    120

```
TGAATAATCC GCTTCTG                                                        137
```

( 2 ) INFORMATION FOR SEQ ID NO: 7:

( i ) SEQUENCE CHARACTERISTICS:
        ( A ) LENGTH: 175
        ( B ) TYPE: nucleic acid
        ( C ) STRANDEDNESS: both
        ( D ) TOPOLOGY: linear ( x i ) SEQUENCE DESCRIPTION: SEQ ID NO: 7:

```
AAGCTTTTAC GGCGCTGAGA TCTTGCATAG GTATTTGACC CTTAAAGAAT AATTACCACA   60
GACGTTCCAT ATTTGGACCG AACTATTCCA TGTGTCGATC TATCTCCAGT ACAGAATATA  120
TGAATAATCC GCTTCTGAAA TTAAGAATAA TTATCATTTA AGGAGTGGT  AAATG       175
```

( 2 ) INFORMATION FOR SEQ ID NO: 8:

( i ) SEQUENCE CHARACTERISTICS:
        ( A ) LENGTH: 534
        ( B ) TYPE: nucleic acid
        ( C ) STRANDEDNESS: both
        ( D ) TOPOLOGY: linear ( x i ) SEQUENCE DESCRIPTION: SEQ ID NO: 8:

```
AAGCTTTTAC GGCGCTGAGA TCTTGCATAG GTATTTGACC CTTAAAGAAT AATTACCACA   60
GACGTTCCAT ATTTGGACCG AACTATTCCA TGTGTCGATC TATCTCCAGT ACAGAATATA  120
TGAATAATCC GCTTCTGAAA TTAAGAATAA TTATCATTTA AGGAGTGGT  AAATGTCCAG  180
ATTCAATCCA TCCCCCGTCA GTTTATCTGT GACACTAGGC TTAATGTTTT CGGCTAGCGC  240
TTTTGCTCAA GACGCGACGA AACGGATGA  AACCATGGTG GTCACTGCGG CGGGATACGC  300
GCAAGTGATT CAAAATGCAC CAGCCAGTAT CAGTGTGATT TCAAGAGAAG ATCTGGAATC  360
TCGCTATTAC CGTGATGTGA CCGATGCGCT AAAAAGCGTA CCGGGTGTGA CAGTCACCGG  420
AGGGGGCGAT ACTACCGATA TCAGCATTCG TGGTATGGGA TCAAACTATA CTCTTATCTT  480
GGTGGATGGT AAGCGCCAAA CCTCACGCCA GACCCGTCCA AACAGCGATG GCCC        534
```

( 2 ) INFORMATION FOR SEQ ID NO: 9:

( i ) SEQUENCE CHARACTERISTICS:
        ( A ) LENGTH: 517
        ( B ) TYPE: nucleic acid
        ( C ) STRANDEDNESS: both
        ( D ) TOPOLOGY: linear ( x i ) SEQUENCE DESCRIPTION: SEQ ID NO: 9:

```
AGATCTTGCA TAGGTATTTG ACCCTTAAAG AATAATTACC ACAGACGTTC CATATTTGGA   60
CCGAACTATT CCATGTGTCG ATCTATCTCC AGTACAGAAT ATATGAATAA TCCGCTTCTG  120
AAATTAAGAA TAATTATCAT TTAAGGAGT  GGTAAATGTC CAGATTCAAT CCATCCCCG   180
TCAGTTTATC TGTGACACTA GGCTTAATGT TTTCGGCTAG CGCTTTTGCT CAAGACGCGA  240
CGAAAACGGA TGAAACCATG GTGGTCACTG CGGCGGGATA CGCGCAAGTG ATTCAAAATG  300
CACCAGCCAG TATCAGTGTG ATTTCAAGAG AAGATCTGGA ATCTCGCTAT TACCGTGATG  360
TGACCGATGC GCTAAAAAGC GTACCGGGTG TGACAGTCAC CGGAGGGGGC GATACTACCG  420
ATATCAGCAT TCGTGGTATG GGATCAAACT ATACTCTTAT CTTGGTGGAT GGTAAGCGCC  480
AAACCTCACG CCAGACCCGT CCAAACAGCG ATGGCCC                           517
```

( 2 ) INFORMATION FOR SEQ ID NO: 10:

( i ) SEQUENCE CHARACTERISTICS:
    ( A ) LENGTH: 439
    ( B ) TYPE: nucleic acid
    ( C ) STRANDEDNESS: both
    ( D ) TOPOLOGY: linear ( x i ) SEQUENCE DESCRIPTION: SEQ ID NO: 10:

```
CGATCTATCT CCAGTACAGA ATATATGAAT AATCCGCTTC TGAAATTAAG AATAATTATC      60
ATTTAAAGGA GTGGTAAATG TCCAGATTCA ATCCATCCCC CGTCAGTTTA TCTGTGACAC     120
TAGGCTTAAT GTTTCGGCT AGCGCTTTTG CTCAAGACGC GACGAAAACG GATGAAACCA      180
TGGTGGTCAC TGCGGCGGGA TACGCGCAAG TGATTCAAAA TGCACCAGCC AGTATCAGTG     240
TGATTTCAAG AGAAGATCTG GAATCTCGCT ATTACCGTGA TGTGACCGAT GCGCTAAAAA     300
GCGTACCGGG TGTGACAGTC ACCGGAGGGG GCGATACTAC CGATATCAGC ATTCGTGGTA     360
TGGGATCAAA CTATACTCTT ATCTTGGTGG ATGGTAAGCG CCAAACCTCA CGCCAGACCC     420
GTCCAAACAG CGATGGCCC                                                  439
```

( 2 ) INFORMATION FOR SEQ ID NO: 11:

( i ) SEQUENCE CHARACTERISTICS:
    ( A ) LENGTH: 42
    ( B ) TYPE: nucleic acid
    ( C ) STRANDEDNESS: single
    ( D ) TOPOLOGY: linear ( x i ) SEQUENCE DESCRIPTION: SEQ ID NO: 11:

```
CCGAATTCTC TAGAGATATC GTGTGGAATT GTGAGCGGAT AA                         42
```

( 2 ) INFORMATION FOR SEQ ID NO: 12:

( i ) SEQUENCE CHARACTERISTICS:
    ( A ) LENGTH: 45
    ( B ) TYPE: nucleic acid
    ( C ) STRANDEDNESS: single
    ( D ) TOPOLOGY: linear ( x i ) SEQUENCE DESCRIPTION: SEQ ID NO: 12:

```
CCAAGCTTCT GCAGCCCGGG ATTAACATT TATGAATCTC CGCCT                       45
```